United States Patent [19]
Rieger et al.

[11] Patent Number: 5,415,838
[45] Date of Patent: May 16, 1995

[54] CARRIER FOR COLORIMETRICALLY DETECTING A GAS

[75] Inventors: Jutta Rieger, Lübeck; Wolfgang Breithaupt, Seedorf; Joachim Marcoll, Lübeck, all of Germany

[73] Assignee: Drägerwerk Aktiengesellschaft, Lübeck, Germany

[21] Appl. No.: 194,272

[22] Filed: Feb. 10, 1994

[30] Foreign Application Priority Data

Feb. 10, 1993 [DE] Germany .................. 43 03 860.3

[51] Int. Cl.⁶ .................................. G01N 21/78
[52] U.S. Cl. .................................. 422/57; 422/58; 422/86; 422/87
[58] Field of Search .................. 422/55, 57, 83, 84–87, 422/91, 82.05, 82.09, 58

[56] References Cited

U.S. PATENT DOCUMENTS

| | | |
|---|---|---|
| 3,676,181 | 7/1972 | Kowalewski . |
| 4,421,719 | 12/1983 | Burleigh ................. 422/57 |
| 4,472,353 | 9/1984 | Moore ................... 422/58 |
| 4,505,985 | 3/1985 | Schmidt et al. . |
| 4,877,683 | 10/1989 | Bragaw, Jr. et al. ........... 428/421 |
| 4,986,110 | 1/1991 | Voss ................. 422/89 X |
| 5,089,232 | 2/1992 | May . |
| 5,147,606 | 9/1992 | Charlton et al. ........... 422/56 |
| 5,364,593 | 11/1994 | Mihaylov et al. ............ 422/57 X |

OTHER PUBLICATIONS

"Flüssigkeiten mikrofein dosieren", by M. Döring, Feinwerktechnik & Messtechnik, vol. 99, No. 11 (1991), pp. 459 to 463.

*Primary Examiner*—Jeffrey R. Snay
*Attorney, Agent, or Firm*—Walter Ottesen

[57] ABSTRACT

One or more reaction zones are formed as channels in a carrier. Each reaction zone is lined with a color indicator and the carrier is improved in that a coating of the reaction zone is realized wherein the coatings are individually changeable and the coating is easily carried out with uniform coating density and, if required, with different indicators. This is achieved with a carrier which is configured as a sandwich-like composite foil which includes a reagent carrier foil which, in turn, is made of a special plastic material. This plastic material can be perfluoroethylene propylene (FEF) which is surface treated by a corona discharge and is then known as FEPc. An especially advantageous embodiment for the reaction zones on the reaction carrier foil is that the reaction partners are applied to the reagent carrier foil in the form of a point matrix applied by a microdrop generator.

12 Claims, 4 Drawing Sheets

CARRIER FOR COLORIMETRICALLY DETECTING A GAS

FIELD OF THE INVENTION

The invention relates to a carrier for one or more reaction zones for colorimetrically detecting gaseous toxic substances. The reaction zones are applied to the carrier so as to have a channel shape. The toxic substances enter into a color reaction with a color indicator when entering the channel. The color indicator is applied to the base surface of the reaction zone as a fining with one or a plurality of channels being applied to the carrier.

BACKGROUND OF THE INVENTION

An arrangement of the above kind is disclosed in U.S. Pat. No. 5,089,232.

Channel-shaped recesses are worked into the known carrier. These recesses each include a color indicator and additional reaction partners for the colorimetric detection reaction. The reaction partners can be identical if each of the channels or they can be different from each other depending upon whether a multiple detection of the same gas component is to be carried out or if a detection of different gas components in air is to be carried out. Each of the channels has at least one inlet opening for the toxic substance to be detected which is either drawn by suction through the channel (through-flow testing tubes) or diffuses into the channel (diffusion testing tubes). Each individual channel thereby operates as a conventional individual testing tube for the colorimetric detection of gaseous components in air.

A multiple measuring device in miniaturized form for the colorimetric detection of gaseous toxic substances is obtained with the arrangement of several channels arranged one parallel to the other on the carrier. The chip-shaped carrier is evaluated by an optoelectronic scanning apparatus. For this purpose, a transmitting and detecting unit is guided at the same elevation and in identical length to each of the individual channels and the light reflected from the colored channel zone is evaluated. The length of the coloration zone provides information as to the concentrations contained in the detection sample or the quantity of time gaseous component to be investigated in dependence upon whether the channels are configured as testing tubes for through flow or as dosimeters for diffusion of the toxic substance.

In the known arrangement, the reaction zones are produced as channels in the base structure of the carrier material and they are in the form of recesses having a shallow depth. The subsequent coating of the channel recesses is possible only under difficult manufacturing conditions and produces an unsatisfactory result with respect to a uniform distribution of the reaction partners, especially of the color indicator along the entire length of the channel recesses. This is especially caused by the introduction of the reaction partners from a liquid emulsion so that a distribution of the reaction partners in a nonuniform density occurs within the channel because of surface tensions of the liquid and because of a nonuniform distribution of the solid constituents in the suspension.

This situation is made still more critical when different reagent carriers for detecting various gaseous components are utilized in the different channels so that also different suspensions are used having different surface tensions and different solid reaction carriers with the solid reaction carriers being distributed in the suspension. A nonuniform distribution of the reaction partners along the channels can result in a fluctuation of the color indication which is not caused by the toxic substance to be detected and leads to an incorrect measuring result.

SUMMARY OF THE INVENTION

It is an object of the invention to improve a carrier of the above-mentioned kind so that an individually changeable application of the reaction zones can be realized which is simple to carry out with the reaction zones having the required indicator materials with uniform coating density and with the indicators being different as may be required. Of special importance is the possibility of a complete conversion of the toxic substance to be detected at the color indicators.

The carrier of the invention is for providing a reaction zone for colorimetrically detecting a gaseous toxic substance and includes: a reagent carrier foil made of perfluoroethylene propylene (FEP) and having a surface treated with a corona discharge; a color indicator containing reagents for entering into a color reaction with the toxic substance; the color indicator being in the form of a surface spread along a predetermined path on the surface to define the reaction zone; foil means covering the reagent carrier foil and defining mutually adjacent side walls along the path so as to cause the side walls and the path to conjointly define a flow channel sealed from the ambient; channel access means for facilitating the penetration of the gas mixture into the flow channel to permit the toxic substance to enter into a color reaction with the color indicator in the reaction zone; and, the reagent carrier foil and the foil means conjointly defining a sandwich-like composite foil.

The elements required for forming the detecting channel are divided into component groups suitable for the preparation of the lining of the channel-shaped reaction zones. These component groups are foils which are present as a composite foil when assembled. With this division, optimized manufacturing technologies can be used for each individual work step. Accordingly, the reaction zone can be formed on the foil-like reagent carrier with know techniques for applying liquids to surfaces. For example, a mask is placed over the reagent carrier foil which predetermines the course or extent of the reaction zones. The exposed cutouts of the mask are filled with the liquid required for the corresponding detection. After evaporation or drying of the solvents, the liquid leaves behind the reaction partners, such as the color indicator, in a solid form.

After the mask is removed, the reaction zones remain as a track on the reaction carrier foil. Problems with different surface tensions or inadequately uniform distribution of the reaction partners along the reaction zones are eliminated since the FEPc foil has especially good adhering characteristics, especially with respect to the adherence of polar reagents.

The channel foils are applied only after drying of the reaction zones is complete and are applied in coincidence with the course of these reaction zones. The channel foils, in turn, define the channel walls next to each individual reaction zone. Here too, the advantage is afforded that the channel structure is worked into a foil because the channel structure can be configured in a simple form as a foil cutout which must not be lined with the indicator. The struts remaining between the cutouts can simply be welded to the reagent carrier foil therebelow to form a unit-so that each two mutually adjacent ones of the channels are closed off sealtight with respect to each other. A cover foil is placed over the channel cutouts and closes off the channel walls. Channel openings are provided at the start and/or at the end of the closed channels formed in this manner. The toxic substance to be detected has access to the reaction zones via these openings. The channel openings can be closed off sealtight by foil membranes which simultaneously constitute part of the additional cover foil placed over the channel foil. This sealing is punctured when the carrier is used as a testing tube. The puncturing can be performed mechanically or by connecting a suction pump to provide a throughflow of the channel as disclosed, for example, in U.S. Pat. No. 5,089,232 incorporated herein by reference.

The especially good adhering characteristics of the FEPc foil can be seen in that the color indicator, which is applied, and the additional reagents required for a color reaction show excellent adhering durability even when there are folds or creases in the foil.

Furthermore, it is possible to apply the reagents to the FEPc foil with a plurality of application processes. These processes include screen processes, spreading on with a brush or printing, spin coating, nebulization or spraying.

Foils of perfluoroethylene propylene are available from various manufacturers. The E. du Pont Company offers these foils under the designation "TEFLON FEP Fluorocarbonfilm Type C". Although glass and conventional TEFLON are suitable as a material for the reagent carrier foil, the above-mentioned characteristics are obtained only by means of the FEF foils treated with a corona discharge. The nature of the corona discharge is disclosed in U.S. Pat. No. 3,676,181 which is likewise herein incorporated by reference. The adhering characteristics and the long service life of the coating are realized with this special foil. It has been surprisingly shown that with the above-mentioned PEP foils, especially the application of polar substances from, for example, an emulsion or by spraying can take place especially easily and without wetting difficulties. This is seen as an unexpected result because FEP is a PTEF compound (known commercially as TEFLON) which is known basically for its non-wetting characteristics.

Foils made of FEPc are furthermore characterized by good welding characteristics whereby a reliable and direct welding of the flow channels to be formed in the composite foil is possible.

The course of the reaction zones can be determined in a simple manner in that an adherence layer is applied to the reagent carrier foil. The adherence layer is made of a precondensate which is obtained pursuant to the sol-gel method disclosed in U.S. Pat. No. 4,505,985 incorporated herein by reference. Silicon gel spherules impregnated, for example, with the color indicator are applied to this precondensate applied in the form of a surface spread. The precondensate can also be printed onto the carrier foil at defined locations defining a point matrix so that thereafter, the impregnated silica gel is only applied at these adhering locations.

One possibility for applying the reagents required for the color reaction in a variation of ways not previously possible is achieved in that the reaction zone is formed as a point matrix. This matrix structure is obtained in that individual drops of a solution or emulsion are applied in a targeted manner along the reaction zone by means of a microdrop generator. The microdrop generator operates pursuant to the principle of a piezoceramic nozzle with the aid of which it is possible to meter liquids as drops in the range of nanoliters (a so-called ink-jet printing method known from commercially available ink-jet printers). An apparatus of this kind is sold in Germany by Microdrop GmbH of Germany and is described in the article of M. Döring entitled "Flüssigkeiten mikrofein dosieren" published in "Feinwerktechnik & Messtechnik 99" (1991) 11, pages 459 to 463.

The drops applied to the reaction zone spread on the reagent carrier foil to form point-shaped spots. It has been shown to be advantageous to select the material FEPc as the reagent carrier foil since the excellent adhering characteristics lead to an almost circular round surface spread of the drop especially with polar liquids so that a smooth closed point edge is obtained. This characteristic is especially useful with respect to a reproducible surface application which can be defined by the size of the drops. Associated herewith is that the liquid quantities can be precisely metered which makes possible a uniform surface distribution of the reagents along the reaction zone whereby a precise color indication with the least possible amount of reagents is provided.

The detection sensitivity can be changed by varying the surface distribution of the individual points on the reaction zone. For example, a linearization of the color display in the course of the diffusion path is obtained by diluting the reagents in the diffusion channel; that is, the dilution is achieved with an ever lesser surface application of reagent drops. When required, also relationships other than linear can be realized between the length of the coloring zone and the quantity/concentration of the toxic substance to be detected by appropriately changing the application of reagent drops. A multiplicity of changes in the sensitivity of detection also for throughflow channels (testing tubes) is possible with such a change of the detection sensitivity by generating a gradient in the point density on the reaction zone. In some cases, it is desired that points on the surface of the reaction zone are so distributed that regions with points are followed by regions without points so that an advance of the coloration within the point region is slow but takes place rapidly from point region to point region.

The application of the reagents to the reaction zone can be carried out in a so-called one-vessel preparation. Here, the components for producing silica gel as carrier substance as well as the reagents (indicator) required for the color reaction are all in a common vessel from which the quantity is taken which is required for the application to the reagent zone. By using one microdrop generator, this vessel can serve directly as a supply vessel from which the quantity required for generating the drops can be taken directly. The so-called sol-gel method has proven to be a suitable preparation process and is described, for example, in U.S. Pat. No. 4,505,985 incorporated herein by reference. Pursuant to this method, a precondensate is first produced to which the components specific for the detection are then added. For example, the composition and production of a solution of this kind for later coating of the reaction zone is given below for the detection of $NH_3$, $NO_2$ and $H_2S$.

Precondensate

Add 20 mL tetramethyloxysilane and 20 mL ethanol to a glass vessel and stir in ice water with a magnetic stirrer. Add 10 mL 0.01m HCl and stir for approximately 5 minutes. The precondensate is further processed only after 24 hours.

The precondensate can be prepared equally well with tetraethyloxysilane in lieu of tetramethyloxysilane. It can then be further processed over a longer time span; that is, the so-called vessel time can be lengthened. The quantity of the acid to be added can be varied as a further parameter for the length of the processing time. Ethanol serves as a diluting component.

The precondensate given above is also suitable as an adhesive agent between the reagent carrier foil and the reagent carrier impregnated with the indicator.

$NH_3$-Coating Solution

A bromophenol blue solution is prepared with 2 g bromophenol blue and 90 mL ethanol and mixed with a magnetic stirrer. 45 mL of the bromophenol blue solution is added to 15 mL of precondensate to form the $NH_3$ coating solution.

$NO_2$-Coating Solution

An o-toluidine solution is prepared by adding 0.425 g o-toluidine to 93 mL ethanol and 7 mL ethylenegycol and stirring with a magnetic stirrer. 42.5 mL o-toluidine solution is added to 10 mL precondensate to form the $NO_2$ coating solution.

$H_2S$-Coating Solution

A Pb-acetate solution is prepared by adding 5 g Pb-acetate to 1.5 mL ethyleneglycol in a 50 mL measuring flask to which a small amount of methanol is added and mixed ultrasonically. The flask is then filled with methanol thereby completing the preparation of the Pb-acetate solution. Now 2.8 mL of the Pb-acetate solution is taken and 32 mL ethanol and 5 mL precondensate added thereto and mixed with a magnetic stirrer.

The above examples can all be prepared as so-called one-vessel preparations; that is, all necessary components can be prepared together in one vessel. Depending upon the variation in components and the concentration, the components must be separately processed for other coating solutions and precondensate and, if necessary, even separately applied to the reagent carrier foil.

If the coating is carried out with a microdrop generator, then several different point matrices can be applied to a single reaction zone in an especially simple manner. Accordingly, a first point matrix can include reagents for the detection of $NH_3$ (ammonia) and a second point matrix can include reagents for detecting $H_2S$. In this way, a double-displaying colorimetric detection device is obtained; or, the second toxic substance display can be applied for eliminating cross sensitivities. The arrangement of different component regions for the point matrices provided there can either be disposed one behind the other in flow direction or parallel to each other in flow or diffusion direction. A further possibility for the arrangement is that a first point matrix can be applied which leaves an adequately wide intermediate space between the individual points so that the points of the second matrix are deliberately placed in these intermediate spaces. The micrometering with the known microdrop generator makes possible a placement of the drops which is precisely reproducible. For this purpose, only a highly precise commercially available X-Y displacer need be positioned along the microdrop generator opening. The X-Y displacer is shifted with the aid of a computer-controlled drive in dependence upon the desired configuration of the point matrix. Not only the position of the individual drops on the reaction zone is important but also the number of drops can be determined which are to be applied to each individual matrix point.

The configuration of the point matrix permits the user to produce an alpha-numeric train which, after the color reaction is completed, is clearly viewable with respect to the background of the reaction carrier foil. This train of characters can be recognized either as a word ("TLV-value exceeded") or as a number ("40 ppm") or as a combination of word and number.

Several component regions lying one behind the other are advantageously provided when no directly indicating color reagent is available for the toxic substance to be detected or the color reagent is not easy to produce so that it is stable for a long period of time. For such cases, a conversion layer is provided upstream of the indicator layer and contains such reagents which chemically decompose the toxic substance to be detected into components of which at least one enters into a color reaction with the downstream indicator layer. The reagents known from testing tube technology can be considered for suitable advance layers (conversion regions) and indicator layers for the toxic substance to be detected.

The component regions can also be arranged one on top of the other in that on the points of a first point matrix, one or more drops can be metered which form a second or, if necessary, a third and an additional point matrix covering the first point matrix. Such an arrangement is, for example, provided for such cases wherein the color indicator only shows its effect after adequate wetting. In this way, the second point matrix would be a moisture emitting layer. The moisture can, for example, be taken from the detecting sample (air moisture) or it is anyway present for an aqueous sample (water analysis). On the other hand, the moisture can be contained ab initio in the porous impregnated carrier by means of the preparation of the silica gel in adequate quantity. A further application provides a drying of the test gas before the substance to be detected reacts with the reagents. In this way, the additional point matrix acts as a dry coating. Another application relates to the detection of $NO_x$. The first point matrix then contains a color indicator for $NO_2$. The second point matrix is in coincidence directly thereover and is subjected to the $NO_x$ and contains an oxidizing agent for converting $NO_x$ to $NO_2$. Such oxidizing agents are, for example, the chromium (VI)-salts and the permanganates.

In addition to the reagent carrier foil, the composite foil still has the channel foil, a protective foil and a base foil. The composite foil assembled in this way is received in fixed position between a carrier upper part and a carrier lower part and so defines a chip-shaped carrier which can be evaluated with the aid of an optical scanning device such as described in U.S. Pat. No. 5,089,232.

An advantageous configuration of the composite foil is a circularly-shaped embodiment which is covered by a correspondingly shaped carrier upper part and carrier lower part. The channel connection is provided at the circular periphery of the composite foil. The reaction channels extend toward the center where a connection for a suction pump is provided. During suction, the reaction layer changes color with more or less intensity in dependence upon the presence of the toxic substance to be detected. The quantity of the toxic substance or its concentration can be estimated with respect to the intensity of coloration with the aid of a color comparison to a color standard. If the central connection is omitted, then the same carrier can be used as a diffusion badge wherein the toxic substance to be detected diffuses from the periphery toward the center. The evaluation then is likewise made as above. The diffusion access can also be central so that the toxic substance diffuses within the badge along the surface of the reaction zone toward the periphery of the circular disc-shaped composite foil.

A foil of FEPc can be advantageously used for such cases wherein a simple badge is directly exposed to the toxic substance to be detected. An FEPc foil serving as a base is stretched or cemented to a carrier. The carrier has a surface facing toward the ambient to which one or more color indicators and additional chemicals are applied and to which the toxic substance to be detected has free access. The color indicators are present in the different regions and the chemicals are required for the colorimetric detection. The indicator becomes colored more or less intensely in dependence upon the quantity of the toxic substance and the duration of exposure.

As an indicator, the known substances utilized in testing tubes can be applied without difficulty because of the surprisingly good adhesion characteristics of the FEPc foil. Also, the patterns mentioned for the channel zones in the composite foil and the coatings alternating with respect to their sensitivity can be applied.

BRIEF DESCRIPTION OF THE DRAWINGS

The invention will now be described with reference to the drawings wherein:

FIG, 1 is a plan view of a chip-shaped carrier having several reaction zones;

Figure 3:
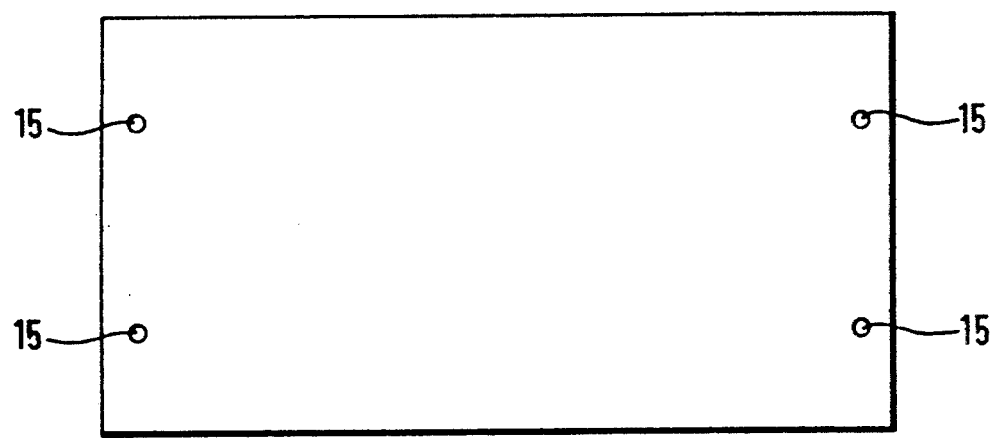
Figure 4:
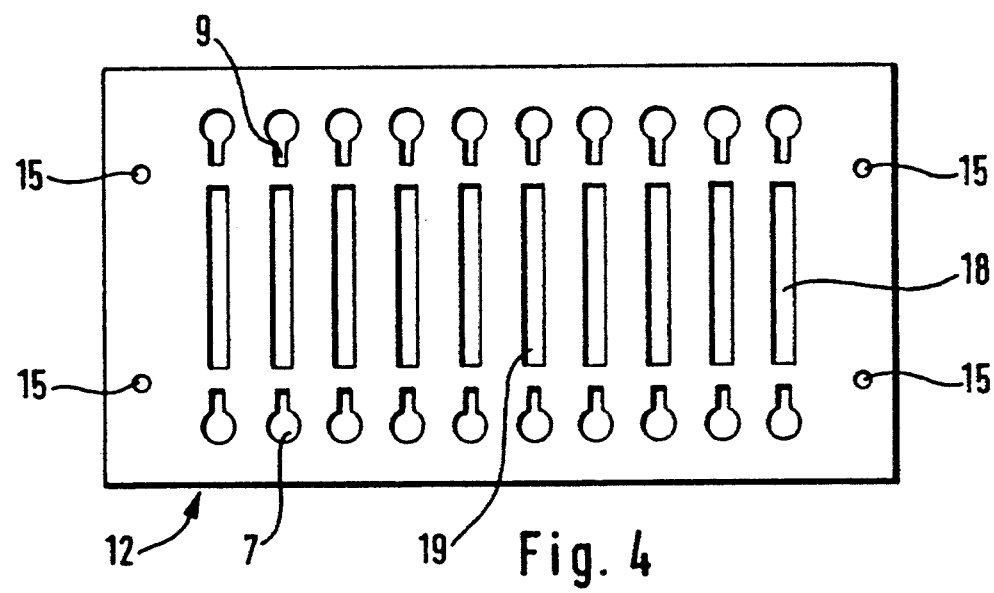
Figure 5:
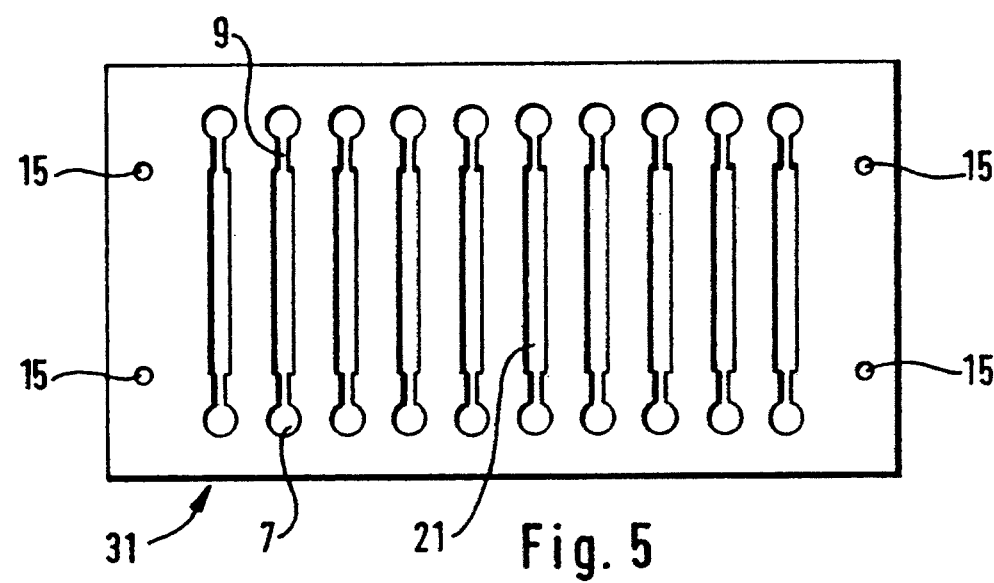
Figure 6:
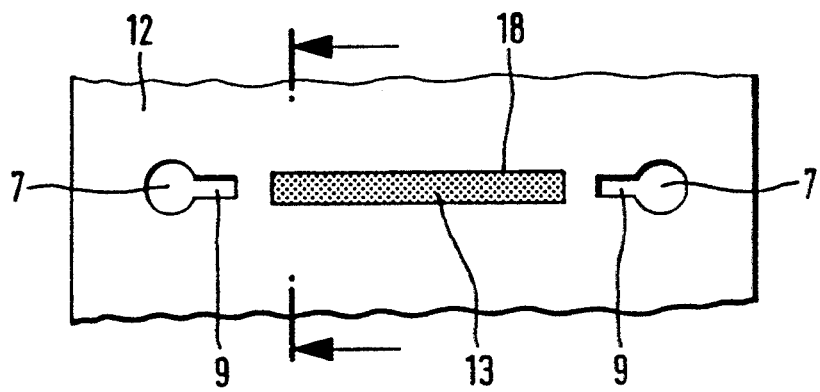
Figure 7:
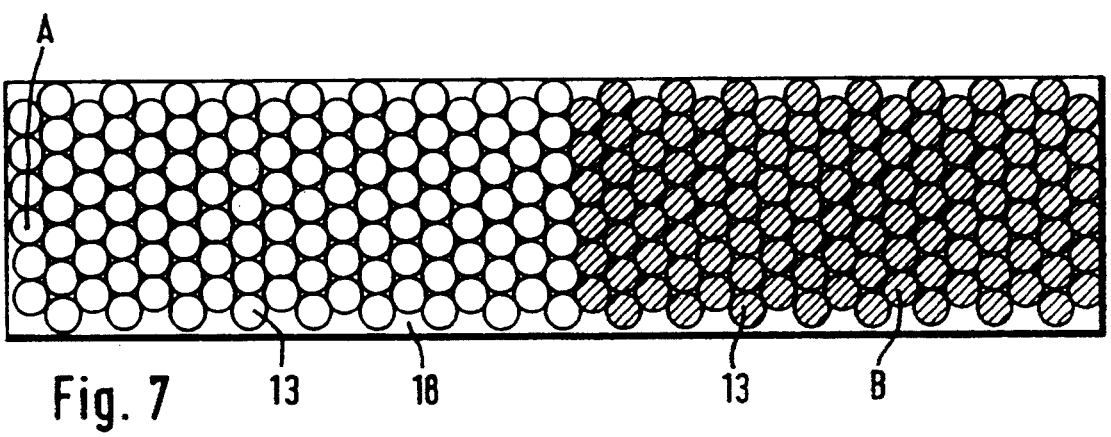
Figure 8:
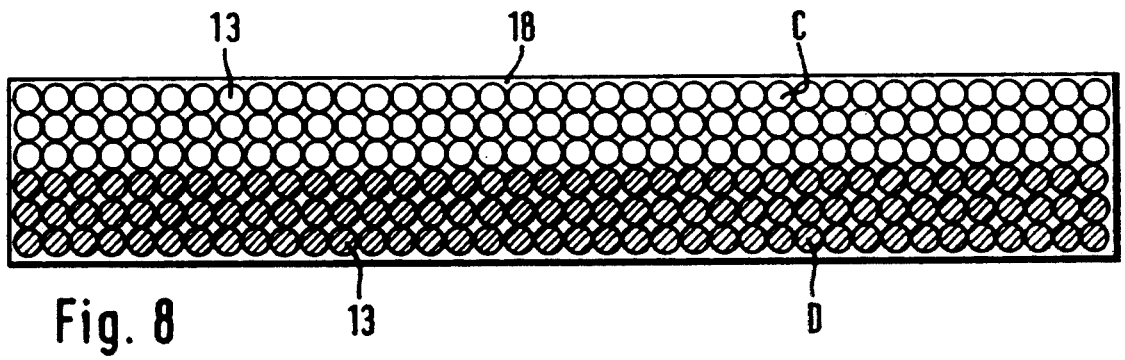
Figure 9:
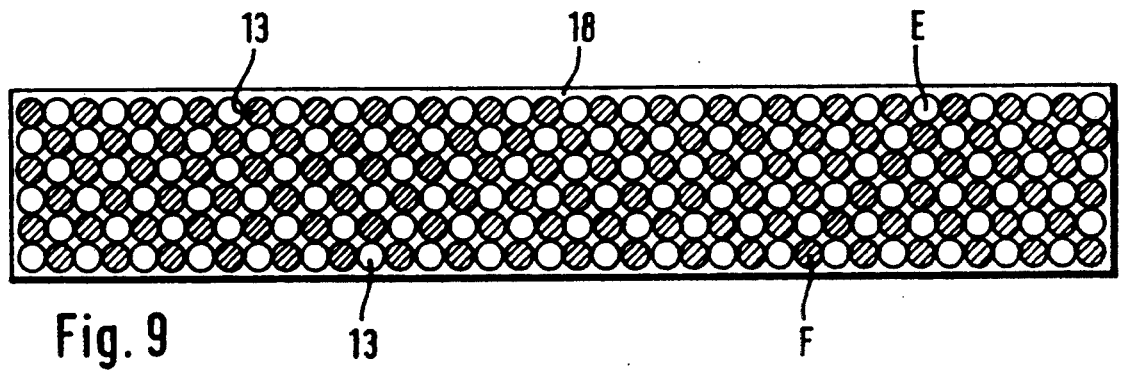
Figure 10:
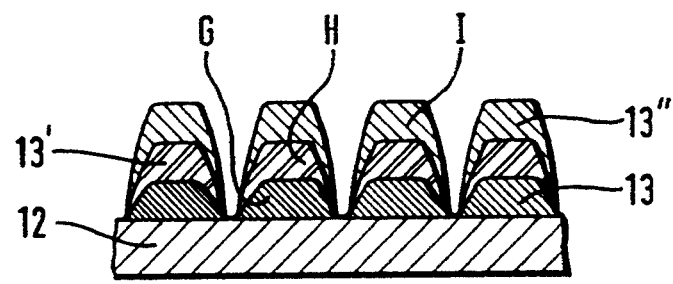
Figure 11:
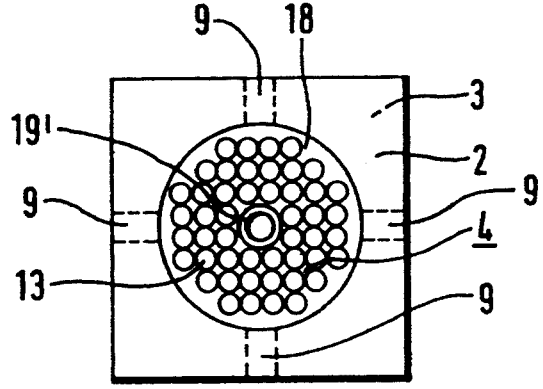
Figure 13:
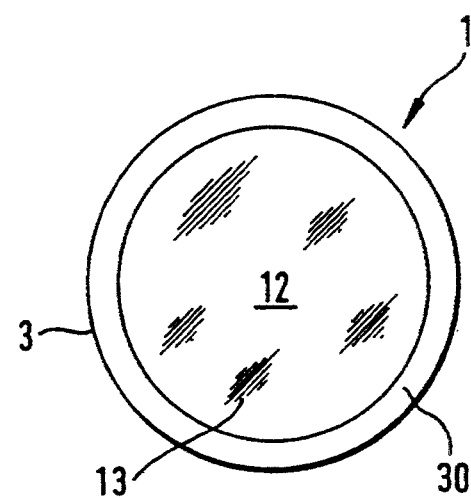
Figure 12:
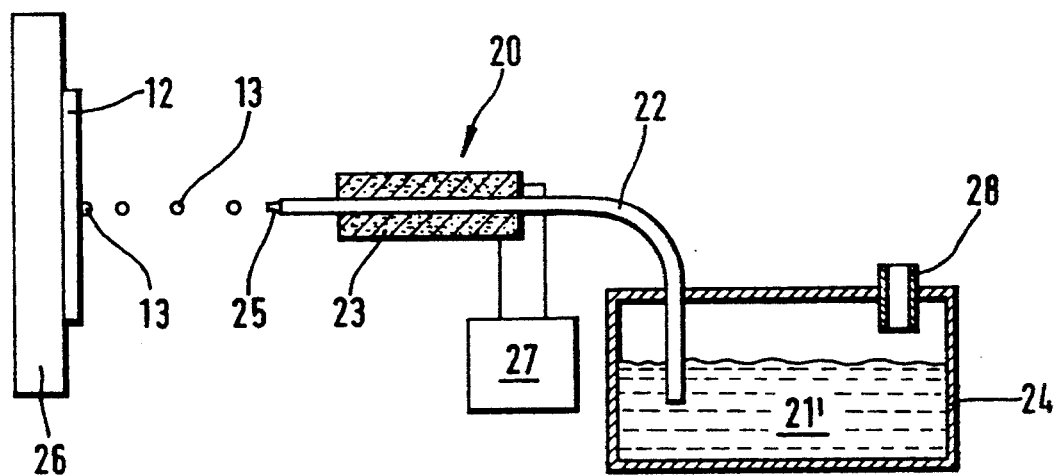

FIG, 2 is a section taken through the carrier of FIG, 1 along a channel-shaped reaction zone;

FIG. 3 is a plan view of a foil which can serve either as the base foil or the cover foil;

FIG. 4 is a plan view of the reagent carrier foil;

FIG. 5 is a plan view of the channel foil;

FIG. 6 is a detail view of a reaction zone in the form of a point matrix;

FIG. 7 is a plan view of a point matrix shown with two component regions disposed one behind the other;

FIG. 8 is a plan view of a point matrix where two component regions are mutually adjacent in the direction of flow;

FIG. 9 is a plan view of a point matrix wherein the component regions are interwoven;

FIG. 10 is a side elevation view showing three component regions of a point matrix lying one atop the other;

FIG. 11 is a plan view of a dosimeter badge;

FIG. 12 is a schematic showing how a microdrop generator is used to apply a point matrix to the reagent carrier foil; and, FIG. 13 is a plan view of a testing badge.

DESCRIPTION OF THE PREFERRED EMBODIMENTS OF THE INVENTION

Figure 1:
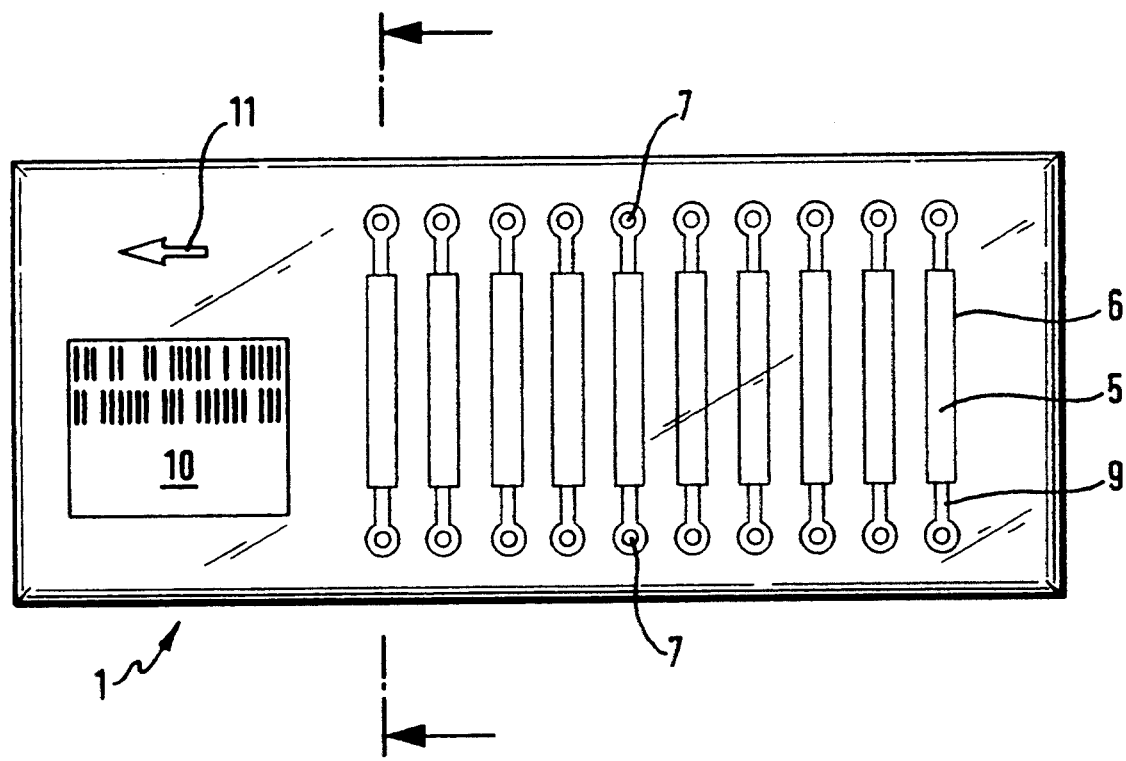
Figure 2:
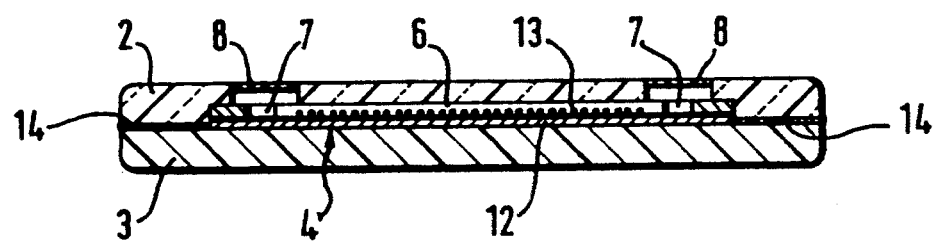

A chip-shaped carrier 1 is shown in FIG. 1 and comprises a carrier upper part 2 and a carrier lower part 3 as shown in FIG. 2. A composite foil 4 is held between the parts (2, 3). The upper part 2 comprises a transparent plastic material and permits ten parallelly running reaction zones 5 to be freely viewed. Each reaction zone is configured as a base surface for a reaction channel 6.

Access openings 7 are provided at the ends of the channels 6 through which the gas mixture to be detected can be drawn through by suction with a pump (not shown) or, in the case of an opening only at one end, so that the gas mixture can migrate to the reaction zone 5 along the channel 6. The access openings 7 are closed with a seal 8 which is punctured for carrying out a measurement. The access openings 7 are connected to the channels 6 via a channel connection 9.

A data field 10 is printed on the surface of the carrier upper part 2 and provides technical information and instructions for the use of the colorimetric detection device. This information can be read either by the user or can be detected by an evaluation unit (not shown) with the aid of a bar code. An evaluation device of this kind is described in U.S. Pat. No. 5,089,232 incorporated herein by reference. A directional arrow 11 indicates which end of the carrier 1 is to be inserted first into the evaluation unit. The data field 10 is read out during the insertion and the information contained therein is transmitted to the evaluation unit. The carrier 1 is inserted so far into the evaluation unit until the first non-used reaction channel 6 reaches the optical evaluation unit. The evaluation unit includes an arrangement of light sources and receivers which, at a specific wavelength, scan the coloration along the course of the reaction zone 5.

At the same time, and after puncturing the seal 8, a pump is connected which draws the gas to be investigated through the channel 6 by suction. The reaction zone 5 colors more or less in dependence upon the content of the gas component in the gas. This coloration is detected by the evaluation unit and is processed to a measured value. An automatic transport to the next-adjacent second channel 6 takes place after evaluation of the first channel 6 is completed. Evaluation of the second channel takes place in the same manner as described. Up to ten different gases, as required, can be investigated and measured in this way.

FIG. 2 is a section view along the length of a channel 6 from the carrier 1 of FIG. 1 with the composite foil 4 containing a reagent carrier foil 12 having a point matrix 13. The point matrix 13 has a defined arrangement of drop spots on the foil 12 which are exposed in the channel 6 to the gas to be investigated. The carrier upper part 2 has the seal 8 located over the access openings 7. The seal 8 is punctured in order to, for example, connect to a pump (not shown) for pumping the gas. The gas to be detected passes via the access openings 7 to the channel 6 and therewith to the point matrix 13 having the applied indicator. The carrier upper part 2 is joined about the periphery to the carrier lower part 3 via an adhesive seam 14 whereby the composite foil 4 is held between the two parts (2, 3).

The indicator can be present impregnated on silica gel spherules in lieu of a point matrix. These spherules can be applied to the reagent carrier foil 12 along the reaction zone 18. The spherules 13 now assume the position of the drops. The remaining parts of the carrier shown in FIG. 2 remain unchanged and can therefore be identified with the same reference numerals. Accordingly, FIG. 2 is exemplary for a point matrix on the reaction zone 18 as well as for a silica-gel coating thereon.

The base foil shown in FIG. 3 comprises only a rectangular simple FEP foil (without pretreatment by means of corona discharge) having four centering or attachment holes 15 in its respective corner regions.

The same base foil 16 can also be utilized as a cover foil 17.

FIG. 4 shows the reagent carrier foil 12 made of FEP, type C (FEPc) which has individual reaction zones 18 running parallel to each other. These reaction zones 18 are coated with the reagents required for the colorimetric detection. The reaction zones 18 can comprise an applied coating 19 which is obtained from a suspension containing all reagents required for the detection of the toxic substance (single-vessel preparation).

The channel foil 31 of FIG. 5 includes breakthroughs which coincide with the course of the reaction zones 18. The breakthroughs serve as channels 21 for the gas components to be investigated. A connection to the access opening 7 is provided to each of the channels 21 via the channel connection 9. The breakthrough of the channel 21 later defines the channel walls when the channel foil 31 is applied to the reagent carrier foil 12. The cover foil 17 is applied to the channel foil and then partitions the channels 21 from each other as well as from the ambient.

An example of a point matrix 13 on the reaction zone 18 is shown in FIG. 6 wherein only a single reaction zone 18 is shown. A plurality of circularly-shaped drops 13 spread on the reagent carrier foil 12 define the point matrix which predetermines the course or extent of the reaction zone 18. Each individual drop 13 is applied to the reagent carrier foil 12 by means of a microdrop generator 20 (see FIG. 12). Each drop contains the reagents required for the color reaction.

A point matrix 13 is shown in FIG. 7 which is subdivided into two component regions (A, B). Component region A lies upstream of component region B when viewed in the flow direction. The upstream component region A comprises drops 13 which contain a chemical for converting a substance to be detected into such components which can be detected in a color reaction by the drops 13 of the component region B. Component region A is therefore a conversion region and component region B is an indicator region.

In FIG. 8, two mutually parallel component regions C and D are shown as a point matrix 13. Each component region (C, D) has drops 13 which each contain an indicator for detecting a different toxic substance.

The component regions (E, F) shown in FIG. 9 are seen as an interwoven point matrix 13. The points 13 of the component region F are inserted into the gaps between the points 13 of the component region E.

These different embodiments of a point matrix 13 are only a selection of many further variations wherein, for example, the component regions are strip-shaped and are mutually adjacent or one behind the other on the reagent carrier foil 12 or points 13 with different reagents alternate within a row and define alternating component regions. In this way, it is clear that the term "component region" has broad meaning and can be widely interpreted.

An embodiment for the arrangement of three component regions (G to I) lying one atop the other is shown in the section view of FIG. 10. A first coating of drops 13 having an indicator for $NO_2$ is applied onto the reagent carrier foil FEPc 12. The first coating is covered by drops 13 of pure silica gel which act as a protective cover (intermediate layer—not shown) for the component region H formed from drops 13 and lying thereabove. The component region H contains an oxidation agent for the conversion of the $NO_x$ to be detected into $NO_2$. The intermediate layer of silica gel is suitable to limit the oxidizing action to the conversion of $NO_x$ to $NO_2$ in order to avoid unwanted changes of the drop 13 in the component region G by the oxidation agent with reference to the stability of the indicator in component region G.

A further component region I is additionally applied over the outer conversion region H. The component region I is formed from drops 13" having reagents having absorption characteristics in order to filter out components from the substance (gaseous or liquid) to be investigated and to exclude these components from participation in the color reaction. These components could otherwise retard or disturb the detection or the detection reaction.

In total, a three-layer coating of component regions (G, H, I) is located on the reaction carrier foil 12. This three-layer coating is formed from a triple-point matrix 13 (13, 13', 13") with three drops of different composition being placed, in coincidence, one atop the other.

The drops (13 to 13") of the individual component regions (G to I) are shown with different hatching to clearly distinguish the different composition of the drops.

FIG. 11 shows another embodiment of the invention configured as a dosimeter badge. The circularly-shaped composite foil is held between a rectangular transparent carrier upper part and a carrier lower part. The reagent carrier foil 12 is covered over its entire surface with a point matrix of drops 13. The reaction zone 18 in this way also extends over the entire surface of the reagent carrier foil 12. Channel openings 9 start from the periphery of the composite foil 4 and the toxic substance to be detected can diffuse through these channel openings into the reaction zone 18. The channel openings 9 are limited to the breakthroughs in the peripheral region between the upper part 2 and the lower part 3 lying below the plane of the drawing. A connection 19' is provided at the center of the carrier upper part 2 to which a suction pump (not shown) can be connected as required in order to utilize the dosimeter as a concentration measuring badge. For this purpose, a defined quantity of sample air is drawn by suction through the badge. The coloration intensity resulting therefrom on the reaction zone 18 is a measure for the concentration of the toxic substance to be detected contained in the sample of air. The central connection 19' is closed sealtight or is omitted ab initio when the badge is used as a dosimeter.

A microdrop generator 20 is depicted in FIG. 12 to show the application of a point matrix 13 to the reagent carrier foil 12. The microdrop generator 20 comprises a capillary tube 22 filled with liquid 21". A piezoceramic element 23 partially jackets the capillary tube 22. The liquid 21" comprises a solution of all reagents required for a desired color reaction and is stored in a supply vessel 24. A small volume of liquid (nl to pl) in the form of microdrops 13 is sprayed onto the reagent carrier foil 12 from a nozzle 25 at the end of the capillary 22 in a manner similar to known ink-jet printers. The foil 12 is mounted on an X-Y indexing device 26 which can be moved by a drive (not shown) in two directions independently of each other in a plane. The X-Y indexing device operates synchronously with the microdrop generator 20 so that a point matrix 13 is produced on the reagent carrier foil 12 with an appropriate control.

The drops are generated in that the piezoceramic element deforms when a voltage is applied by the generator control 27 to the electrodes of this element whereby a very rapid pressure increase is generated in the incompressible liquid. This pressure increase propagates itself along the capillary 22 to the nozzle 25. A fine liquid column leaves the nozzle 25 at a very high acceleration and immediately forms a drop 13. The lost liquid volume is resupplied from the supply vessel 24 by capillary forces. The vessel 24 has a vent and refill opening 28.

An especially simple embodiment of the testing badge is shown in FIG. 13. The plan view shows a carrier 1 comprising only a carrier lower part 3 as well as a peripheral edge 30 on which a foil 12 of FEPc is attached with adhesive. The foil 12 is coated with a color indicator as a reaction zone 13. The reaction zone 13 is subjected directly to the toxic substance to be detected. As soon as this substance comes into contact with the color indicator, the toxic substance enters into a color reaction with the color indicator whereby the indicator becomes colored with more or less intensity.

It is understood that the foregoing description is that of the preferred embodiments of the invention and that various changes and modifications may be made thereto without departing from the spirit and scope of the invention as defined in the appended claims.

What is claimed is:

1. A carrier for providing a reaction zone for colorimetrically detecting a gaseous toxic substance, the carrier comprising:
  a reagent carrier foil made of perfluoroethylene propylene (FEP) and having a surface treated with a corona discharge;
  a color indicator containing reagents for entering into a color reaction with said toxic substance;
  said color indicator being in the form of a plurality of surface spreads along respective predetermined mutually separate paths on said surface of said reagent carrier foil to define a corresponding plurality of mutually separate reaction zones each independent of the other;
  said paths having respective locations where said reaction zones begin;
  a channel foil covering said reagent carrier foil and having a plurality of cutouts formed therein to define a plurality of pairs of mutually adjacent side walls for respective ones of said paths to define a plurality of flow channels separate from each other;
  a plurality of mutually separate access channels at corresponding ones of said locations for facilitating the separate penetration of said gas mixture into said flow channels to permit said toxic substance to enter into respective color reactions with said color indicator in said reaction zones to provide separate linear colorations which advance along said paths in dependence upon the length of exposure to said gaseous toxic substance;
  a cover foil covering said channel foil for sealing said flow channels with respect to each other and the ambient; and,
  said reagent carrier foil, said channel foil and said cover foil conjointly defining a sandwich composite foil.

2. The carrier of claim 1, further comprising an adherence layer applied to said surface of said reagent carrier foil; a multiplicity of silica gel spherules; said color indicator being impregnated in said spherules; and, said spherules being applied to said adherence layer.

3. The carrier of claim 1, further comprising a solid upper part and a solid lower part conjointly defining an interface; and, said composite foil being held between said parts at said interface.

4. The carrier of claim 1, said color indicator being distributed on said surface of said reagent carrier foil in the form of a multiplicity of individual drops applied to said surface of said reagent carrier foil in a predetermined pattern with microdrop generator from a suspension containing said reagents; and, said drops being disposed on said surface in a point matrix defining said path.

5. The carrier of claim 4, wherein said suspension is a coating solution obtained pursuant to a sol-gel process.

6. The carrier of claim 4, each said reaction zone being subdivided into a plurality of component regions arranged one behind the other in flow direction; and, said component regions having respective reaction partners different from each other.

7. The carrier of claim 4, each said reaction zone being subdivided into a plurality of component regions arranged one parallel to the other in flow direction; and, said component regions having respective reaction partners different from each other.

8. The carrier of claim 4, each said reaction zone being subdivided into first and second component regions arranged along said path so as to be parallel to each other; said first component region including said color indicator with a first reagent to produce a first color reaction; and, said second component region including said color indicator with a second reagent to produce a second color reaction.

9. The carrier of claim 4, each said reaction zone being subdivided into first and second component regions and said first component region being disposed upstream of said second component region; said second component region including said color indicator as a reaction partner and said first component region including a reagent for entering into a reaction with said toxic substance to produce a reaction product which can enter into a color reaction with said color indicator.

10. The carrier of claim 4, said multiplicity of drops being a first multiplicity of drops; said first multiplicity of drops defining a component region disposed along said path as said point matrix containing said reagents for detecting said toxic substance; and, a second component region in the form of an additional multiplicity of drops on top of corresponding ones of said drops of said first multiplicity of drops.

11. A carrier for providing a reaction zone for colorimetrically detecting a gaseous toxic substance, the carrier comprising:
  a reagent carrier foil made of perfluoroethylene propylene (FEP) and having a surface treated with a corona discharge;
  a color indicator containing reagents for entering into a color reaction with said toxic substance;
  a channel foil covering said reagent carrier foil and having cutouts formed therein to define a plurality of pairs of mutually adjacent side walls to define a plurality of flow channels separate from each other;
  a cover foil covering said channel foil for sealing said flow channels with respect to each other and the ambient;

said reagent carrier foil, said channel foil and said cover foil conjointly defining a sandwich composite foil;

said composite foil being a circular member defining a center and having a circumferential periphery;

said color indicator being in the form of a surface spread over all of said surface of said reagent carrier foil thereby causing all of said surface to define a reaction zone; and, said flow channels extending from said circumferential periphery toward said center for conducting said gaseous toxic substance to said surface spread and said reaction zone to cause a coloration in dependence upon the concentration of said gaseous toxic substance.

12. A carrier for providing a reaction zone for colorimetrically detecting a gaseous toxic substance, the carrier comprising:

a reagent carrier foil made of perfluoroethylene propylene (FEP) and having a surface treated with a corona discharge;

a color indicator containing reagents for entering into a color reaction with said toxic substance;

a channel foil covering said reagent carrier foil and having a cutout formed therein to define mutually adjacent side walls to define a flow channel;

a cover foil covering said channel foil for sealing said flow channel with respect to the ambient;

said reagent carrier foil, said channel foil and said cover foil conjointly defining a sandwich composite foil;

said composite foil being a circular member defining a center and having an outer periphery;

said color indicator being in the form of a surface spread over all of said surface of said reagent carrier foil thereby causing all of said surface to define a reaction zone; and, said flow channel extending from said center to said outer periphery.

* * * * *

UNITED STATES PATENT AND TRADEMARK OFFICE
CERTIFICATE OF CORRECTION

PATENT NO. : 5,415,838

DATED : May 16, 1995

INVENTOR(S) : Jutta Rieger, Wolfgang Breithaupt and Joachim Marcoll

It is certified that error appears in the above-identified patent and that said Letters Patent is hereby corrected as shown below:

In the title page, in the Abstract, item [57], line 11: delete "FEF" and substitute -- FEP -- therefor.

In column 1, line 12: delete "fining" and substitute -- lining -- therefor.

In column 1, line 23: delete "if" and substitute -- in -- therefor.

In column 1, line 45: delete "time" and substitute -- the -- therefor.

In column 3, line 3: delete "unit-so" and substitute -- unit so -- therefor.

In column 3, line 35: delete "FEF" and substitute -- FEP -- therefor.

In column 3, line 41: delete "PEP" and substitute -- FEP -- therefor.

In column 7, line 34: delete "FIG, 1" and substitute -- FIG. 1 -- therefor.

In column 7, line 36: delete "FIG, 2" and substitute -- FIG. 2 -- therefor.

In column 7, line 36: delete "FIG," (second occurrence) and substitute -- FIG. -- therefor.

UNITED STATES PATENT AND TRADEMARK OFFICE
CERTIFICATE OF CORRECTION

PATENT NO. : 5,415,838
DATED : May 16, 1995
INVENTOR(S) : Jutta Rieger, Wolfgang Breithaupt and Joachim Marcoll It is certified that error appears in the above-identified patent and that said Letters Patent is hereby corrected as shown below:

In column 10, line 53: delete "21"." and substitute -- 21'. -- therefor.

In column 10, line 55: delete "21"" and substitute -- 21' -- therefor.

Signed and Sealed this

Twenty-fifth Day of July, 1995

*Attest:*

BRUCE LEHMAN

*Attesting Officer*      *Commissioner of Patents and Trademarks*